United States Patent [19]

Hughes

[11] Patent Number: 5,068,887
[45] Date of Patent: Nov. 26, 1991

[54] DENTAL X-RAY ALIGNMENT DEVICE

[76] Inventor: John R. Hughes, 4140 E. La Paloma Dr., Tucson, Ariz. 85718

[21] Appl. No.: 618,080

[22] Filed: Nov. 26, 1990

[51] Int. Cl.$^5$ .............................................. G03B 42/02
[52] U.S. Cl. ..................................... 378/170; 378/206
[58] Field of Search .................................. 378/206, 170

[56] References Cited

U.S. PATENT DOCUMENTS

| | | |
|---|---|---|
| 2,581,431 | 1/1952 | Nelsen . |
| 2,659,824 | 11/1953 | Burnham . |
| 3,102,957 | 9/1963 | Slauson . |
| 3,628,021 | 12/1971 | MacDonald . |
| 3,745,344 | 7/1973 | Updegrave . |
| 3,831,031 | 8/1974 | Barrett . |
| 3,864,576 | 2/1975 | Stevenson . |
| 4,012,638 | 3/1977 | Altschuler . |
| 4,100,408 | 7/1978 | Marshall . |
| 4,428,029 | 1/1984 | Baliozian . |
| 4,442,533 | 4/1984 | Lescrenier . |
| 4,887,286 | 12/1989 | Seidenberg . |

*Primary Examiner*—Craig E. Church
*Attorney, Agent, or Firm*—J. Michael McClanahan

[57] ABSTRACT

A dental x-ray alignment device is described for attachment to the extension tube of the x-ray unit. The device has a cylindrical conical frustum exterior shape with a central opening adapted to frictionally reside on the extension tube. An annularly shaped conical cavity is formed in the sidewalls of the cylindrical conical frustum, the cavity being open on one end joining the front face of the frustum. A plurality of light emitting sources are situated in the base or bottom of the frustum to emit light from the open end of the cavity. The light is projected onto the patient's face to circumscribe the x-ray beam pattern for certainty of x-ray beam placement during procedures. In an alternate embodiment, the invention is incorporated into the coupler and extension tube normally attached to the x-ray unit head. In this embodiment, an annularly shaped open-ended cavity is formed around a cylinder replacing the extension tube with the plurality of light emitting sources situated in the base of the cavity to project a circle of light onto the patient's face and jaw.

22 Claims, 1 Drawing Sheet

DENTAL X-RAY ALIGNMENT DEVICE

BACKGROUND OF THE INVENTION

1. Field of the Invention

The field of the invention is devices attached to dental x-ray unit machines extension tubes to more accurately locate the x-ray pattern upon a patient's face.

2. Description of the Related Art

In the field of dentistry, it often becomes necessary for the dentist or technician to take x-rays of a portion or all of a patient's teeth for purposes of determining dental carries, misalignment of teeth, problems with teeth roots, and for other reasons. This is commonly accomplished by the placement of x-ray sensitive film within the patient's mouth and interiorly to the teeth. Most often, the film is held in place for the x-ray procedure by the patient clamping their teeth down upon a perpendicularly protruding paper tab centrally located on the flat side of the film. The x-ray unit machine emitting head is placed proximate the patient's jaw immediately outside the skin overlying the location of the film.

Dental x-ray units are conventionally equipped with extension tubes to be used as guides in establishing the direction of the x-ray beam pattern conically ejected by an emitter situated in the x-ray unit head. Generally the x-ray emitter is situated proximate the point of attachment of the extension tube to the x-ray unit head.

It is not uncommon for the operator to misdirect or misalign the x-ray beam when accomplishing x-ray procedures in which case only a portion of the film is exposed to the x-rays (and thus not all teeth filmed). In such case, the operator must perform the x-ray procedures again. This is not only costly in terms of film used but also subjects the patient to repeated doses of x-rays. Further, the operator may not know that the film was not properly exposed until after it is developed, which may be a period of time after the procedure was done. This necessitates repeating the procedure with its attendant duties at a later time, making for inefficient expenditure of time and at an increased cost.

While the operator generally has no difficulty knowing where on the face of the patient the film is situated within the month, yet it would be an obvious great help to the operator if they knew the extent of the x-ray beam pattern.

There are various devices which are known to the Applicant for accomplishing the alignment of dental x-ray unit heads and some are as follows. Nelsen, in U.S. Pat. No. 2,581,431, adds an additional tubular extension to the supplied extension tube and in this tubular extension, places cross hairs at its terminal end together with a string situated along the longitudinal center. Then the terminal end of the device is placed proximate the patient's face. By sighting along the string, the path of the x-rays is determined. Seidenberg, in U.S. Pat. No. 4,887,286, discloses a device which attaches to the extension tube of the dental x-ray unit, the device utilizing an upper and a lower light emitting unit to project two beams of light outwardly defining the beam. The light emitting units are pre-focused bulbs which may include an integral lens. The device is so constructed so that the light emitting units are located within the extension tube and potentially in the path of the x-ray beam although by being on the top and bottom, they would interrupt the beam such that the exposure of tooth roots would be affected.

Burnham, in U.S. Pat. No. 2,659,824, situates a pair of focused light beam sources on opposite sides of the dental x-ray unit head such that the coincidence of the two light beams indicate the center of the x-ray beam. Lastly, Updegrave, in U.S. Pat. No. 3,745,344, discloses a lead-lined rectangular collimating tube attached to the dental x-ray unit head which in turn has attached at its terminal end a bite block. Alignment is achieved since the patient moves to a correct position to utilize the bite block.

While the above devices shown in the patents cited apparently accomplish the purpose intended, yet all have shortcomings of one type or another, either being bulky, difficult to use, or as in the case of Seidenberg, have the potential of being in the path of the x-ray beam.

It is readily apparent therefore that improvements to the art of dental x-ray alignment devices are needed inasmuch as with all the devices which are known and available, yet they have not been adopted in widespread use.

Accordingly, there is a need for a simple and inexpensive device which efficiently and readily aligns the x-ray beam pattern upon the face of the patient in order that the operator may be absolutely sure that the x-ray beam is correctly aimed to fully expose the entire film.

SUMMARY OF THE INVENTION

The embodiment of the inventive dental x-ray alignment device described consists of a cylindrical conical frustum with a central opening adapted to reside on the terminal end of the extension tube provided with the dental x-ray unit. The device aligns the x-ray pattern upon the face of a patient such that the x-ray pattern will completely expose the film held interiorly to the patient's mouth and thus show all teeth in front of the film. In particular, the subject dental x-ray alignment device central opening situated longitudinally through the frustum is adapted to frictionally slip over and thereby be secured to the extension tube or nose-cone of the dental x-ray unit. A snug fit is desired such that the central opening or bore of the frustum is in alignment with the nose-cone or extension tube. If desired, a portion of the central opening may be stepped outward a small distance to form a shoulder to seat against the outer peripheral rim of the extension tube.

The alignment device places a circle of light upon the face of the patient. In the preferred embodiment, the diameter of the circle of light is approximately the same diameter as the x-ray beam pattern at the recommended distance from the patient's face.

The circle of light is generated by a series of light emitting sources situated at the closed bottom or base of a first annularly shaped conical plenum or cavity formed in the sides of the cylindrical conical frustum, the annularly shaped conical cavity concentric about the invention's central opening. The annular conical cavity is formed from two spaced apart converging cylindrical walls, the cylindrical walls directionally converging (although not meeting) to the front of the alignment device. The annular conical cavity is open at the front of the alignment device and closed near the rear of the frustum except for a plurality of spaced apart small openings in the base of the cavity to accommodate the light sources. Various types of light sources may be utilized, such as incandescent bulbs, laser emitting diodes, or the like situated within these small openings. For convenience of routing electrical wires connecting to the light emitting sources, a second annular cavity is formed immediately behind the base of the cavity. This annular cavity communicates with the annular conical cavity through the plurality of small openings. For that matter, a circular neon tube could reside in this annular cavity, its light passing through the small openings.

Access to the second annular cavity at the rear of the cylindrical conical frustum is gained by removal of an annular disc shaped back plate or disc which covers the cavity and through which passes the electrical leads powering the light emitting sources.

In an alternate embodiment of the invention, the manufacturer supplied extension tube and coupling on the x-ray unit head is removed and the invention incorporated into a new extension tube and coupling so that a circularly shaped light beam is emitted which would be coaxial with the prior extension tube, if it were present. More particularly, a first annularly shaped cylindrical cavity open at the front is formed around a cylindrical wall which duplicates the prior extension tube, the cavity having a plurality of light sources at its base. As part of the construction of the alternate embodiment, the portion of the manufacturer supplied coupling having the collimating opening which defines the resultant x-ray pattern and the internal threads by which the coupler attaches to the x-ray unit head are incorporated. Like the preferred embodiment, access to the light sources which provide light for the circularly shaped light beam is obtained by means of a second annularly shaped cavity formed immediately behind the first annularly shaped cylindrical cavity.

Accordingly, it is an object of the subject invention to provide a dental x-ray alignment device which provides the dental technician/operator an indication of the x-ray beam pattern.

It is another object of the subject invention to provide a dental x-ray alignment device for determination of location of the x-ray beam which device is easily added to the conventional dental x-ray units and which is easily operated.

It is still a further object of the subject invention to provide a dental x-ray alignment device which places a lighted circle upon the patient's face generally outlining the pattern of the x-ray beam.

Other objects of the invention will in part be obvious and will in part appear hereinafter. The invention accordingly comprises the apparatus possessing the construction, combination of elements, and arrangement of parts which are exemplified in the following detailed disclosure, and the scope of the invention which will be indicated in the claims.

BRIEF DESCRIPTION OF THE DRAWINGS

For further understanding of the features and objects of the subject invention, reference should be had to the following detailed description taken in connection with the accompanying drawings wherein.

In various views, like index numbers refer to like elements.

DETAILED DESCRIPTION OF THE PREFERRED EMBODIMENT

Figure 1:
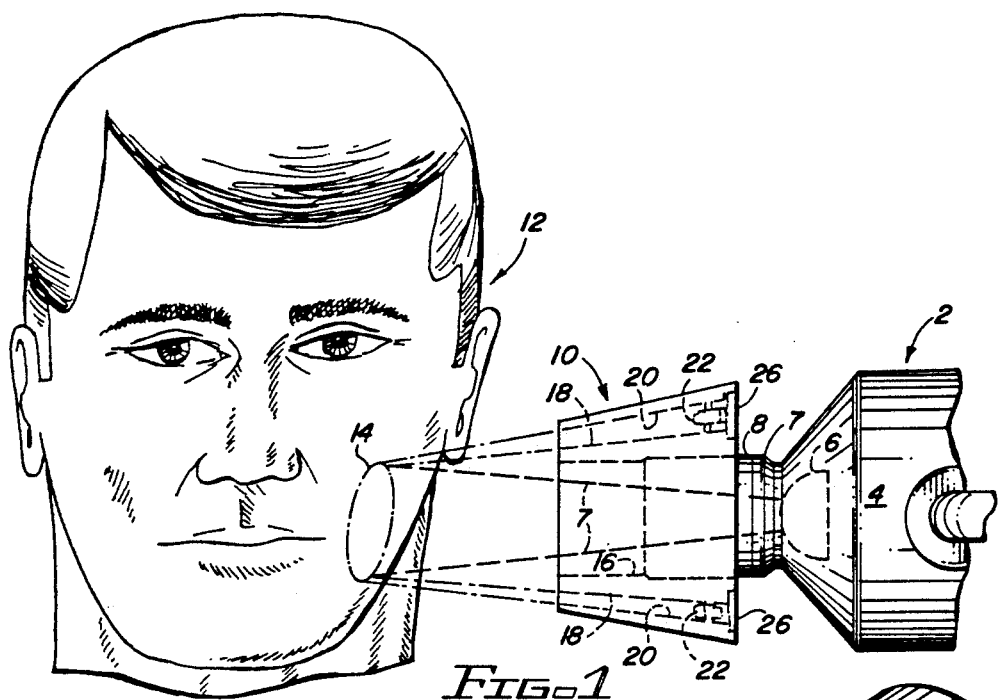
FIG. 1 is a side view of the subject alignment device attached to the dental x-ray unit.

Referring now to FIG. 1, a side view of the subject dental x-ray alignment device is shown in use with a patient. Commencing at the right and moving left, dental x-ray unit 2 is shown in partial view, showing however a portion of x-ray head 4, the x-ray emitting element 6, coupler 7 threaded onto x-ray head 4, and extension tube 8 attached to coupler 7, all of which is supplied by the manufacturer with the machine. Shown ejecting from the x-ray emitting element 6 are x-rays 7, the x-rays taking a conical shaped pattern defined by a circular collimating opening (not shown) situated centrally in coupler 7 and designed to penetrate the side of the patient 12 face, through teeth interiorly, and on to the film held by the patient inside their mouth. Attached to extension tube 8 is the subject dental x-ray alignment device 10, the invention placing a circle of light upon the person's face and within which the x-ray pattern is centrally contained. Shown on the jaw of patient 12 is the ring of light 14 which defines the x-ray beam pattern.

The dental x-ray alignment device 10 shown in FIG. 1 comprises a cylindrical shaped conical frustum cylinder having a centrally situated longitudinal central bore with a front opening and means to project a circle of light consisting in part of a first annularly shaped conical cavity or plenum which is open at the front face of the alignment device. The rear or base portion of the annular cavity is terminated into a plurality of light emitting sources consisting of incandescent bulbs, laser emitting diodes, or other similar light sources as desired. Power to these light emitting sources is supplied through electrical wires (not shown) which in turn connect with an appropriate power source.

More specifically, shown in FIG. 1 in dotted fashion is the longitudinal central bore 16 which in the preferred embodiment has straight non-tapered parallel sides however, approximately ½ of its length is stepped outwardly from a first diameter to a second slightly larger diameter to circularly encompass a sufficient portion of extension tube 8 to frictionally secure the alignment device to the extension tube and to assure that the alignment device is aligned with extension tube 8. The shoulder formed by outwardly stepping the second diameter of central opening 8 is shown resting against the outer peripheral rim of extension tube 8.

Figure 4:
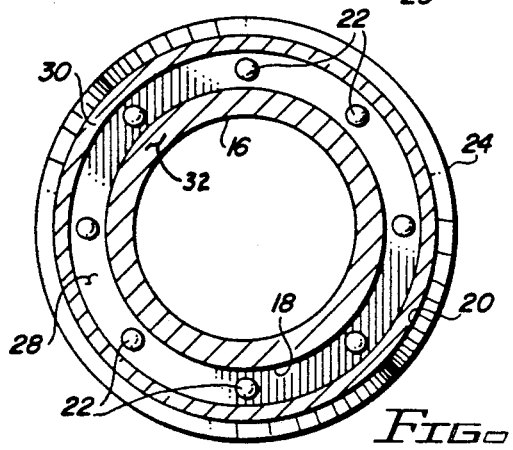
FIG. 4 is a sectional view of the subject inventive dental x-ray alignment device taken along line 4—4 shown in FIG. 3.

Forming the tapered sides of the first annularly shaped conical plenum or cavity formed within the wall thickness of the subject device is first or inside cylindrical tapered surface 18 which runs from the front of the invention to the rear and to the closed base or bottom of the cavity, the base being a radially directed annularly shaped side of web 28 (shown in FIG. 4). Spaced apart from surface 18 is second or outside converging cylindrical tapered surface 20. Not only are these two cylindrical tapered surfaces concentric and converging to the front face of the invention with respect to each other, but both are angled in acute angles with respect to central bore 16. As indicated above, the first and second cylindrical tapered surfaces exit to the front end of the alignment device 10 to form an open circular front or annular opening which confines the light as much as possible to narrowing annular ring 14 shown in FIG. 1 projecting upon the side of the patient's face.

To generate the circle of light which ultimately falls upon the face of the patient, at the bottom of the cavity formed by the converging first and second cylindrical surfaces 18 and 20 is situated a plurality of light emitting sources 22.

It is realized that the circle of light which falls on the face of the patient will follow the form of the annular outlet of the annularly shaped cavity formed by first and second cylindrical surfaces 18 and 20 and will be brightest in the middle of the light forming the circle and will fall off in intensity rapidly in the in and out radial directions. Due to the sloping or tapered sides of the first annularly shaped cavity formed by first and second cylindrical surfaces 18 and 20, the light will be generally conformed to the resultant circle. It is intended that the ring of light should, at the normal distance that the x-ray unit is held from the patient's face, approximate the spread of the conical x-ray pattern at that distance, but in any case, the center of the light circle will also be the center of the x-ray pattern. Clearly this depends upon the manufacturer of the x-ray unit assuring that the x-ray extension tube 8 in FIG. 1 is co-aligned with the pattern of x-ray beam 7.

Figure 2:
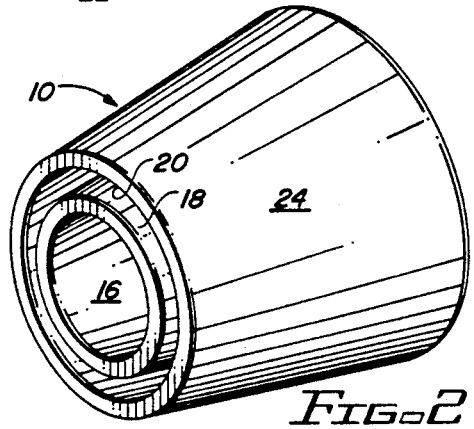
FIG. 2 is a perspective view of the subject inventive dental x-ray alignment device.

Referring now to FIG. 2, a perspective view of the subject dental x-ray alignment device 10 is shown detailing in particular its front light emitting end or face, the device essentially constructed of two concentric annularly formed thin wall cylinders joined at the rear end. Firstly, first cylindrical tapered surface 18 is shown together with the spaced apart and encompassing second cylindrical surface 20. These surfaces form the annularly shaped conical cavity interiorly to alignment device 10, at the bottom of which resides the light emitting sources and at its front face is provided the opening for the circle shaped emitted light rays. The conical frustum shaped cylinder which comprises the alignment device has as its outer surface, tapered cylindrical surface 24. Lastly, central opening 16, which is of constant diameter through approximately the first ½ the length, is shown, central opening 16 then increasing slightly to encompass with a rather snug fit the external cylindrical surface of the x-ray emitting extension tube 8 (FIG. 1).

Figure 3:
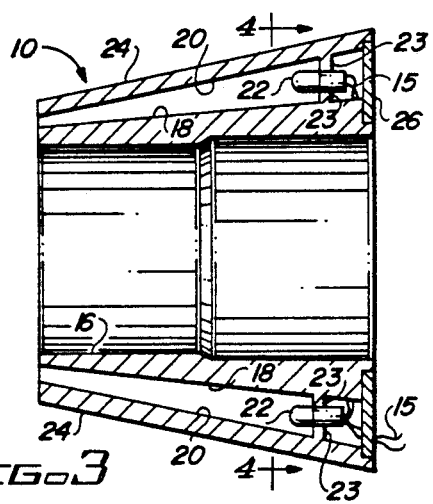
FIG. 3 is a cross sectional view of the subject inventive dental x-ray alignment device.

Shown in FIG. 3 is a cross-sectional view taken through dental x-ray alignment device 10 showing in detail the various cylindrical surfaces which comprise the invention. Starting from the outside, outer cylindrical surface 24 is shown tapering from the rear to the front followed by concentric second cylindrical tapered surface 20 and concentric first cylindrical tapered surface 18. As indicated earlier, first and second cylindrical tapered surfaces 18 and 20 comprise the sides of the first annularly shaped conical cavity which opens to the front face of the cylinder, the opening helping to form the resultant circle of light which is illuminated on the face of the patient, the light emitting sources 22 being at the bottom or base of the cavity. Shown in FIG. 3 is the outstanding small circular openings 23 through base web 28 (FIG. 4) which help secure light emitting sources 22 in place. Light emitting sources 22 may be contained in a socket which threads into threads formed in circular opening 23 or may be secured by any number of means well known within the engineering art.

In the examples shown in FIG. 3, light emitting sources 22 may be incandescent bulbs or, they may be laser emitting diodes outputting a coherent source of light. In the case of laser emitting diodes, the ring or circle formed on the face of the patient would comprise a circle of dots, as many dots as there are light sources. In the case of incandescent bulbs, the light from each bulb would tend to blend into its neighbor and distinct light spots would not be noticeable, or if noticeable, only slightly. Of course, prefocused light sources which employ lenses could also be used as could single tubes filled with a gas which fluoresces or ionizes upon the application of electrical power, such as the mercury vapor lamps or neon lamps. The openings for the plurality of light sources are formed in the structural web that resides at the bottom of the first annularly shaped conical cavity formed by opposite closed bases of the first and second annular shaped cavities. This web is the structural means holding the resultant outer cylinder to the resultant inner cylinder. The light sources must be placed in and through these various spaced openings in this annular web. To the rear of light sources 22 are shown the electrical wires 15 which supply the electrical power.

Immediately behind or to the rear of the annular base or bottom of the cavity formed by the annular base web is a second cavity formed of an outside and inside cylindrical concentric surfaces and a radially directed annular base, the second cavity being annular in shape and receiving the bottom portion of the light emitting source. If a annular ring of light such as a neon tube were employed, the tube itself would reside in this cavity with its generated light then emitting through the small openings 23. It is realized of course that while the greater portion of the web securing the two solid cylinders to each other may have openings therethrough, these openings need not be circular.

Seen immediately inwardly the first annularly shaped conical cavity formed by first and second cylindrical tapered surfaces 18 and 20 is the annular cylinder having as its interior bore central opening 16. As indicated earlier, 16 is for the most part a constant single diameter which enlarges approximately midway through the length of the alignment device 10 to a size to frictionally encompass the outside cylindrical surface of the x-ray emitting extension tube 8.

Lastly, seen is rear cap 26 comprising an annular shaped thin disc plate which may be removed as needed to gain access to the second annular cavity holding light emitting sources 22. This annular plate is friction-fitted into the cavity formed by shoulders placed in the rear annularly shaped face of the invention. If desired, these shoulders may be slightly undercut to help secure annular rear cap 26. In such case, the shoulders would then be notched in two or three places in order to allow a technician to slip a screwdriver into such notch and under a edge of the rear cap 26 to pry it off.

Referring now to FIG. 4, a view is taken through the sectional line 4—4 of the inventive dental x-ray alignment device 10 shown in FIG. 3. Here is immediately visible the plurality of eight spaced apart light emitting sources 22 which protrude through each of the circular openings 23 (FIG. 3) formed in web 28 which connects the outer tapered cylinder 30 to inner tapered cylinder 32. Variously shown in FIG. 4 are the ends of the cylindrical surfaces, starting with the internal bore, central opening 16, first cylindrical tapered surface 18, second cylindrical tapered surface 20, and lastly, outer tapered cylindrical surface 24.

Figure 5:
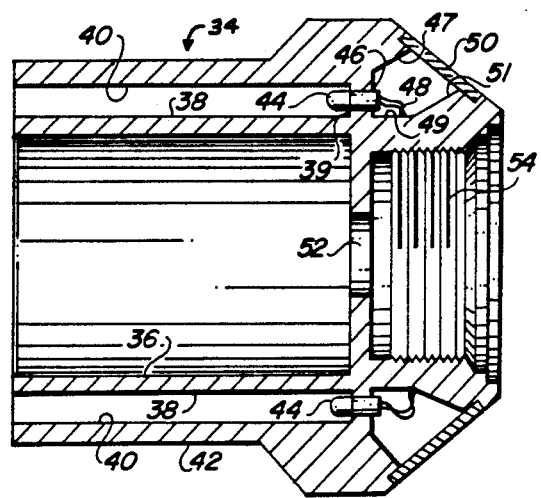
FIG. 5 is a sectional view of an alternate embodiment of the subject inventive dental x-ray alignment device.

FIG. 5 is a sectional view of an alternate embodiment of the invention wherein extension tube 8 and coupler 7 (FIG. 1) have both been removed from the x-ray unit head 4 and the invention incorporated into these two units so there is only a single element (instead of three elements). First referring to FIG. 1, with respect to the coupler and extension tube delivered by the manufacturer with the dental x-ray unit, the coupler has internal threads at its rear circular end which screw onto external threads located at the output of the x-ray unit head. The coupler is short and cylindrical in shape and at its circular front opening are located external threads adapted to receive internal threads of extension tube 8. Concentrically interiorly to coupler 7 is a circular reduced diameter collimating opening which, in combination with the x-ray emitter 6, defines the conical shaped patterns of x-rays emitting from the x-ray unit head.

In FIG. 5 is shown the invention incorporated into the coupler and extension tube whereby it replaces these elements and with its internal threads, screws directly on to the external threads of the x-ray unit head. More particularly and referring to FIG. 5, shown is the alternate embodiment of the subject invention comprising cylinder 34 which is so sized to have substantially the same longitudinal central bore diameter at its front part as the inside diameter of the manufacturer supplied extension tube 8 shown in FIG. 1. Immediately radially outside of central bore cylindrical wall 36 are the two cylindrical surfaces or walls together with a first radially directed annularly shaped base defining an annularly shaped cylindrical cavity becoming the means through whose front end light emits, namely inside cavity cylindrical surface 38 and outside cavity cylindrical surface 40 and annularly shaped base 39. Outside the alternate embodiment cylinder 34 is its outer cylindrical surface 42.

Proceeding to the right and to the rear of cylinder 34, at annular base 39 of the annular cylindrical cavity formed by inside and outside cavity cylindrical surfaces 38 and 40 respectively are light sources 44, here shown two of the plurality of light sources. As was the case in the preferred embodiment of the invention, light sources 44 protrude through a circular opening formed in the wall or web connecting the inside and outside cavity cylindrical surfaces 38 and 40, and which form cavity base 39. The rear portion of light sources 44 extend into a smaller rear or second annular cavity immediately behind the forward or first annular cylindrical cavity which receives the light from light sources 44. This smaller rear cavity is made up of three cylindrically shaped surfaces 47, 49, and 51 respectively, and a second radially directed annularly shaped base 46 and opens to the rear face of cylinder 34. Electrical wires 48 connect all the light sources together to a supply of electrical power. Covering the rear annular cavity is annular plate 50, plate 50 adapted to be secured in a snap fit over the rear annular cavity.

Also seen in FIG. 5 is the collimating opening 52 which, like its predecessor in the manufactured supplied coupling, defines the conical pattern of the x-rays. Lastly, internal threads 54 are formed in the rear opening of the alternate embodiment, these threads adapted to mate with the external threads on the emitting end of x-ray unit 4 (FIG. 1).

In the alternate embodiment it is intended that the annular cylindrical cavity formed by cylindrical surfaces 38 and 40 should be parallel as well as coaxial or concentric with the inside cylindrical wall 36 so that there is no spreading or converging of the circle of light which would be emitted out the annularly shaped open front face of the invention. This circle of light will define the central location of the x-ray beam pattern so that this pattern will be centrally located within or at about the circle of light emitted at the distances that the x-ray unit is normally held away from the patient's face.

While a preferred embodiment of the invention has been shown and described, it is appreciated that other such embodiments of the invention are possible and that there is no intent to limit the invention by such disclosure, but rather that it is intended to cover all modifications and alternate embodiments falling within the spirit and the scope of the invention as defined in the appended claims.

I claim:

1. An alignment device for attachment to the extension tube of a dental x-ray unit to align the extension tube through which a pattern of x-rays is emitted to a patient's jaw, the device comprising:
   a cylinder adapted to operably attach to the extension tube, said cylinder having a front face and a rear face; and
   means operably attached to said cylinder to project a circle of light to the patient's jaw in alignment with the x-ray pattern emitted from the extension tube, said means including a first cylindrical surface formed in said cylinder, a second cylindrical surface also formed in said cylinder, said first cylindrical surface concentric to said second cylindrical surface, and a first radially directed annularly shaped base joining said first and second cylindrical surface, said first and second cylindrical surface and said first base defining a first annularly shaped cavity with an open circular front situated at the front face of said cylinder.

2. The alignment device as defined in claim 1 wherein said means projecting a circle of light includes a light emitting source proximate said base of said cylinder whereby light emitted by said light source projects from the front circular opening of the cavity.

3. The alignment device as defined in claim 2 wherein said cylinder includes a longitudinal central bore, said bore adapted to operably frictionally reside on the extension tube.

4. The alignment device as defined in claim 3 wherein said cylinder central bore has a first diameter, said first diameter stepped to a larger second diameter interiorly to said central bore, said cylinder second diameter central bore frictionally residing on the extension tube, and the extension tube abutting said central bore first diameter.

5. The alignment device as defined in claim 4 wherein said first cylinder central bore is concentric to said first and second cylindrical surfaces.

6. The alignment device as defined in claim 5 further including a third cylindrical surface formed in said cylinder, a fourth cylindrical surface also formed in said cylinder, said third cylindrical surface concentric to said fourth cylindrical surface, and a second radially directed annularly shaped base joining said third and fourth cylindrical surfaces, said third and fourth cylindrical surfaces and said second base defining a second annularly shaped cavity with an open circular outlet situated at the rear face of said cylinder.

7. The alignment device as defined in claim 6 wherein said second base of said cylinder is proximate said first base of said cylinder.

8. The alignment device as defined in claim 7 wherein said second base of said cylinder includes an opening communicating with said first base of said cylinder, said opening receiving said light emitting source whereby light emitted by said light emitting source is emitted into the first annularly shaped cavity and out its front opening.

9. The alignment device as defined in claim 8 wherein said cylinder further includes an annularly shaped disc plate, said disc plate removably attaching to said cylinder rear face to cover the second annularly shaped cavity circular outlet.

10. The alignment device as defined in claim 9 wherein said second base of said cylinder includes a plurality of openings communicating with said first base of said cylinder into the first annularly shaped cavity.

11. The alignment device as defined in claim 10 further including a plurality of light sources, said plurality of light sources received by said plurality of openings communicating said second base of the second annularly shaped cavity to said first base of the first annularly shaped cavity.

12. The alignment device as defined in claim 11 wherein said first cylindrical surface and said second cylindrical surface are so oriented to directionally converge to said front face of said cylinder.

13. The alignment device as defined in claim 12 wherein said cylinder comprises a cylindrical conical frustum.

14. The alignment device as defined in claim 13 wherein said light emitting source comprises laser emitting diodes.

15. The alignment device as defined in claim 13 wherein said light emitting source comprises incandescent electrical bulbs.

16. An alignment device for attachment to a dental x-ray unit head to align the pattern of x-rays emitted from the head to a patient's jaw, the device comprising:
a cylinder adapted to operably attach to the dental x-ray unit head, said cylinder having a longitudinal central bore with a front face and a rear face; and
means operably attached to said cylinder to project a circle of light to the patient's jaw in alignment with the x-ray pattern emitted from the x-ray unit head, said means including a first cylindrica surface formed in said cylinder, a second cylindrical surface also formed in said cylinder, said first cylindrical surface concentric to said second cylindrical surface, and a first radially directed annularly shaped base joining said first and second cylindrical surface, said first and second cylindrical surface and said first base defining a first annularly shaped cavity with an open circular front situated at the front face of said cylinder.

17. The alignment device as defined in claim 16 wherein said means projecting a circle of light include a light emitting source approximate said first base of said cylinder whereby light emitted by said light source projects from the open circular front of the first annularly shaped cavity.

18. The alignment device as defined in claim 17 wherein said cylinder longitudinal central bore includes a front central opening and a rear central opening, said front opening permitting the emission of the x-rays and said rear opening operably attaching to the dental x-ray unit head.

19. The alignment device as defined in claim 18 wherein said first and said second cylindrical surfaces are parallel and said cylinder front central opening is concentric with and parallel to said first and second cylindrical surfaces.

20. The alignment device as defined in claim 19 further including a third, fourth, and fifth cylindrical surface formed in said cylinder, said third, fourth, and fifth cylindrical surface each concentric around said rear central opening, and a second radially directed annularly shaped base joining said third and fourth cylindrical surfaces, said third, fourth, and fifth cylindrical surface and said second base defining a second annularly shaped cavity with an open circular front situated at the rear of said cylinder.

21. The alignment device as defined in claim 20 wherein said second base of the second annularly shaped cavity is proximate said first base of the first annularly shaped cavity, and said second base of the second annularly shaped cavity includes an opening communicating with said first base of the first annularly shaped cavity, said opening adapted to receive said light emitting source whereby said light emitted by said light emitting source is emitted into the first annularly shaped cavity and out its open circular front.

22. The alignment device as defined in claim 21 wherein said second base of said cylinder includes a plurality of openings communicating with said first base of said cylinder into the first annularly shaped cavity, and further including a plurality of light sources, said plurality of light sources received by said plurality of openings.

* * * * *